(12) United States Patent
Srinivas et al.

(10) Patent No.: US 8,124,801 B2
(45) Date of Patent: Feb. 28, 2012

(54) PROCESS OF MANUFACTURING OF FATTY ACID ALKYL ESTERS

(75) Inventors: Darbha Srinivas, Pune (IN); Paul Ratnassamy, Pune (IN); Sanjeevani Amrit Pardhy, Pune (IN); Thirumalaiswamy Raja, Pune (IN); Shilpa Shirish Deshpande, Pune (IN); Vijay Vasant Bokade, Pune (IN); Kashinath Joti Wagmare, Pune (IN); Arshia Altaf Lalljee, New Delhi (IN); Surya Prakash Babu, New Dlehi (IN); Karukappadath Kunjimoideen Abdul Rashid, Ernakulam (IN); Khaliji Anas, Ernakulam (IN); Chennampilly Ummer Aniz, Ernakulan (IN)

(73) Assignee: Benefuel Inc., Chicago, IL (US)

( * ) Notice: Subject to any disclaimer, the term of this patent is extended or adjusted under 35 U.S.C. 154(b) by 159 days.

(21) Appl. No.: 12/490,802

(22) Filed: Jun. 24, 2009

(65) Prior Publication Data

US 2009/0326252 A1 Dec. 31, 2009

(30) Foreign Application Priority Data

Jun. 24, 2008 (IN) .......................... 1520/DEL/2008
Jun. 12, 2009 (IN) .......................... 1214/DEL/2009

(51) Int. Cl.
*C11C 3/04* (2006.01)
*C11C 3/10* (2006.01)
*C07C 67/02* (2006.01)

(52) U.S. Cl. ........ 554/169; 554/174; 554/173; 554/157; 554/227; 560/234

(58) Field of Classification Search .................. None
See application file for complete search history.

(56) References Cited

U.S. PATENT DOCUMENTS

| | | |
|---|---|---|
| 3,278,457 A | 10/1966 | Milgrom |
| 5,482,908 A | 1/1996 | Le-Khac |
| 5,525,126 A | 6/1996 | Basu et al. |
| 5,536,883 A | 7/1996 | Le-Khac |
| 5,578,090 A | 11/1996 | Bradin |
| 5,713,965 A | 2/1998 | Foglia et al. |
| 5,908,946 A | 6/1999 | Stern et al. |
| 6,015,440 A | 1/2000 | Noureddini |
| 6,147,196 A | 11/2000 | Stern et al. |
| 6,398,707 B1 | 6/2002 | Wu et al. |
| 6,399,800 B1 | 6/2002 | Haas et al. |
| 6,479,689 B1 | 11/2002 | Tojo et al. |
| 6,489,496 B2 | 12/2002 | Barnhorst et al. |
| 6,624,286 B2 | 9/2003 | Hofmann et al. |
| 6,642,399 B2 | 11/2003 | Boocock |
| 6,696,583 B2 | 2/2004 | Koncar et al. |
| 6,712,867 B1 | 3/2004 | Boocock |
| 6,768,015 B1 | 7/2004 | Luxem et al. |
| 6,822,105 B1 | 11/2004 | Luxem et al. |
| 6,835,858 B1 | 12/2004 | De Jonge et al. |
| 6,855,838 B2 | 2/2005 | Haas et al. |
| 6,878,837 B2 | 4/2005 | Bournay et al. |
| 6,960,972 B2 | 11/2005 | Nakamura et al. |
| 7,122,688 B2 | 10/2006 | Lin et al. |
| 7,211,681 B2 | 5/2007 | Furuta |
| 7,312,355 B2 | 12/2007 | Corma Canos et al. |
| 7,482,480 B2 | 1/2009 | Srinivas et al. |
| 2003/0004363 A1 | 1/2003 | Koncar |
| 2004/0044240 A1 | 3/2004 | Grosch et al. |
| 2005/0027137 A1 | 2/2005 | Hooker |
| 2007/0004599 A1 | 1/2007 | Srinivas et al. |
| 2007/0083056 A1 | 4/2007 | Srinivas et al. |
| 2007/0083062 A1 | 4/2007 | Srinivas et al. |
| 2007/0093380 A1 | 4/2007 | Srinivas et al. |
| 2007/0167642 A1 | 7/2007 | Oku et al. |
| 2007/0282118 A1 | 12/2007 | Gupta et al. |
| 2008/0110082 A1 | 5/2008 | Maliszewski et al. |
| 2010/0005708 A1 | 1/2010 | Estevez Company et al. |

FOREIGN PATENT DOCUMENTS

| | | |
|---|---|---|
| WO | 00/05327 | 2/2000 |
| WO | 2004/048311 | 6/2004 |
| WO | 2004/085583 | 10/2004 |
| WO | 2008122790 | 10/2008 |

OTHER PUBLICATIONS

Nakagaki et al. "Use of anhydrous sodium molybdate as an efficient heterogeneous catalyst for soybean oil methanolysis," Applied Catalysis A: General, 2008, pp. 267-274; Elsevier.

Sunita et al. "Synthesis of biodiesel over zirconia-supported isopoly and heteropoly tungstate catalysts," Catalysis Communications, Aug. 19, 2007, pp. 696-702; Elsevier.

Alsalme et al. "Heteropoly acids as catalysts for liquid-phase esterification and transesterification," Applied Catalysis A: General, Jul. 31, 2008, pp. 170-175; Elsevier.

Pesaresi et al. "Cs-doped H4SiW12O40 catalysts for biodiesel applications," Applied Catalysis A: General, Mar. 13, 2009, pp. 50-58; Elsevier.

Zieba et al. Methanolysis of Castor Oil Catalysed by Solid Potassium and Cesium Salts of 12-Tungstophosphoric Acid, Catalysis Letters, Oct. 7, 2008, pp. 183-194; Springer.

(Continued)

*Primary Examiner* — Yate K Cutliff
(74) *Attorney, Agent, or Firm* — Meyertons, Hood, Kivlin, Kowert & Goetzel, P.C.; Eric B. Meyertons

(57) ABSTRACT

Processes for preparation of fatty acid alkyl esters are described herein. The processes include contacting fatty acid glycerides with alcohols in the presence of a catalyst separating the reaction products from the catalyst, and separating the fatty acid alkyl esters from the reaction products. The catalyst includes a metal from Group VIB of the Periodic Table and an element from Group VA of the Periodic Table.

59 Claims, No Drawings

OTHER PUBLICATIONS

Cao et al. "Biodiesel Production From High Acid Value Waste Frying Oil Catalyzed by Superacid Heteropolyacid" Biotechnology and Bioengineering, Mar. 7, 2008, pp. 93-100; Wiley InterScience.

Caetano et al. "Esterification of free fatty acids with methanol using heteropolyacids immobilized on silica," Catalysis Communications, Mar. 25, 2008; Elsevier.

Cardoso et al., "Investigation on the Esterification of Fatty Acids Catalyzed by the H3PW12O40 heteropolyacid," J. Am. Oil Chem. Soc., Mar. 26, 2008, pp. 555-560: Springer, AOCS press.

Rao et al. "Structure-activity relations in Cs-doped heteropolyacid catalysts for biodiesel production," Journal of Catalysis, Apr. 25, 2007, pp. 226-234; Elsevier.

Chai et al. "Transesterification of Vegetable Oil to Biodiesel using a Heteropolyacid Solid Catalyst," Adv. Synth. Catal., 2007, pp. 1057-1065; Wiley InterScience.

Rao et al. "Zirconium phosphate supported tungsten oxide solid acid catalysts for the esterification of palmitic acid," Green Chemistry, Jul. 12, 2006, pp. 790-797; The Royal Society of Chemistry.

Lotero et al., "The Catalysis of Biodiesel Synthesis," Catalysis, 2006, pp. 41-83;The Royal Society of Chemistry.

Kim et al., "Transesterification of vegetable oil to biodiesel using heterogeneous base catalyst," Catalysis Today, Jul. 30, 2004, pp. 315-320; Elsevier.

Watkins et al. "Li-CaO catalysed tri-glyceride transesterification for biodiesel applications," Green Chem, Jul. 5, 2004, pp. 335-340; The Royal Society of Chemistry.

Tesser et al. "Kinetics of Oleic Acid Esterification with Methanol in the Presence of Triglycerides," Ind. Eng. Chem. Res. Sep. 17, 2005, pp. 7968-7982.; American Chemical Society.

Mbaraka et al. "Design of multifunctionalized mesoporous silicas for esterifcation," Journal of Catalysis, Dec. 23, 2004, pp. 365-373; Elsevier.

Schuchardt et al. "Transesterification of soybean oil catalyzed by alkylguanidines heterogenized on different substituted polystyrenes," Journal of Molecular Catalysis A: General, Jan. 2, 1996, pp. 37-34; Elsevier.

Noureddini et al, "A Continuous Process for the Conversion of Vegetable Oils into Methyl Esters of Fatty Acids," Journal Am. Oil Chem. Soc., 1998, pp. 1775-1783; AOCS press.

Leclercq et al. "Transesterifcation of Rapeseed Oil in the Presence of Basic Zeolites and Related Solid Catalysts," J. Am. Oil Chem. Soc., 1998, pp. 1161-1165; AOCS press.

Lopez et al., "Transesterification of triacetin with methanol on solid acid and base catalysts," Applied Catalysis A: General, Sep. 22, 2005, pp. 97-105; Elsevier.

Kiss et al, "Solid Acid Catalysts for Biodiesel Productio—Towards Sustainable Energy," Adv. Synth. Catalysis, 2006, pp. 75-81, Wiley InterScience.

Suppes et al. "Transeterification of soybean oil with zeolite and metal catalysts," Applied Catalysis A: General, 2004, pp. 213-223; Elsevier.

Bancquart et al. "Glycerol transesterification with methyl stearate over solid basic catalysts I. Relationship between activity and basicity," Applied Catalysis A: General, 2001, pp. 1-11; Elsevier.

Gryglewicz, "Rapeseed oil methyl esters preparation using heterogeneous catalysts," Bioresource Technology, 1999, pp. 249-253; Elsevier.

Ma et al. "Biodiesel production: a review," Bioresource Technology, 1999, pp. 1-15; Elsevier.

PCT, "International Search Report and Written Opinion," for International Application No. PCT/US2009/048393, mailed Jan. 29, 2010, 15 pages.

Suppes et al., "Transesterification of soybean oil with zeolite and metal catalysts," Applied Catalysis A: General, 2004, pp. 213-223, Elsevier.

Dmytryshyn et al., "Synthesis and characterization of vegetable oil derived esters: evaluation for their diesel additive properties," Bioresource Technology, 2004, pp. 55-64, Elsevier.

Vicente et al., "Integrated biodiesel production: a comparison of different homogeneous catalysts systems," Bioresource Technology, 2004, pp. 297-305, Elsevier.

Furuta et al., "Biodiesel fuel production with solid superacid catalysis in fixed bed reactor under atmospheric pressure," Catalysis Communications, 2004, pp. 721-723, Elsevier.

Soumanou et al., "Improvement in lipase-catalyzed synthesis of fatty acid methyl esters form sunflower oil," Enzyme and Microbial Technology, 2003, pp. 97-103, Elsevier.

Khare et al., "Immobilization of Rhizopus japonicus lipase on celite and its application for enrichment of docosahexaenoic acid in soybean oil," Food Chemistry, 2000, pp. 153-157, Elsevier.

Siler-Marinkovic et al., "Transesterification of sunflower oil in situ," Fuel, 1998, pp. 1389-1391, Elsevier.

Schuchardt et al., "Transesterification of Vegetable Oils: a Reivew," J. Braz. Chem. Soc., 1998, pp. 199-210.

Suppes et al., "Calcium Carbonate Catalyzed Alcoholysis of Fats and Oils," JAOCS, 2001, pp. 139-145, AOCS Press.

Darnoko et al., "Kinetics of Palm Oil Transesterification in a Batch Reactor," JAOCS, 2000, pp. 1263-1267, AOCS Press.

Corma et al., "Catalysts for the Production of Fine Chemicals," Journal of Catalysis, 1998, pp. 315-321, Academic Press.

Brat et al., "Fatty Acid Composition of Margarines and Cooking Fats Available on the Czech Market," Journal of Food Composition and Analysis, 2000, pp. 337-343, Academic Press.

Abreu et al., "Utilization of metal complexes as catalysts in the transesterification of Brazilian vegetable oils with different alcohols," Journal of Molecular Catalysis A: Chemical, 2004, pp. 29-33, Elsevier.

Abreu et al., "New multi-phase catalytic systems based on tin compounds active for vegetable oil transesterificaton reaction," Journal of Molecular Catalyst A: Chemical, 2005, pp. 263-267. Elsevier.

Shimada et al., "Enzymatic alcoholysis for biodiesel fuel production and application of the reaction to oil processing," Journal of Molecular Catalysis B: Enzymatic, 2002, pp. 133-142, Elsevier.

Watanabe et al., "Conversion of degummed soybean oil to biodiesel fuel with immobilized Candida antarctica lipase," Journal of Molecular Catalysis B: Enzymatic, 2002, pp. 151-155, Elsevier.

Barnwal et al., "Prospects of biodiesel production from vegetable oils in India," Renewable & Sustainable Energy Reviews, 2005, pp. 363-378, Elsevier.

U.S. Patent and Trademark Office, "Communication" for U.S. Appl. No. 11/394,133, mailed Dec. 22, 2008.

U.S. Patent and Trademark Office, "Office Communication" for U.S. Appl. No. 11/394,133, mailed May 19, 2008.

U.S. Patent and Trademark Office, "Office Communication" for U.S. Appl. No. 11/394,133, mailed Sep. 25, 2007.

U.S. Patent and Trademark Office, "Communication" for U.S. Appl. No. 11/442,651, mailed Apr. 14, 2009.

PROCESS OF MANUFACTURING OF FATTY ACID ALKYL ESTERS

BACKGROUND

1. Field of the Invention

The present invention relates to a process for making esters. More particularly, it relates to a process for making fatty acid alkyl esters.

2. Brief Description of Related Art

Bio-diesel typically include long chain, fatty acid alkyl esters produced from vegetable oils or animal fats by transesterification of the triglycerides with lower alcohols (for example, methanol and/or ethanol). Bio-lubricants may be prepared through transesterification of triglycerides with $C_5$ to $C_{12}$ alcohols. In recent years, there is a growing tendency towards using vegetable-based products in many formulations as substitutes for the petroleum-based products. This prompts researchers that are more concerned about environmental protection and greenhouse gas effects to develop bio-based products. These new bio-based products derived from vegetable and plant products, such as soybean, sunflower, and rapeseed etc, are renewable, biodegradable, less environmental hazardous, and safer to handle. Similarly, other renewable sources of triglycerides include rendered animal fats and waste cooking oils from commercial food production. Rendered animal fats and waste cooking oils may be sulfur-free and are used in automobile applications, mechanical engine applications, cosmetic applications, and soaps.

The heating value of vegetable oil is similar to that of fossil fuel (for example, diesel), but the direct use of vegetable oils in the diesel engines is limited by some of their physical properties. For example, the viscosity of vegetable oil is about 10 times the viscosity of diesel fuel. Transesterification is one among the four major available treatments, which is most commonly employed to improve the fuel value and lubricant utility of triglycerides.

Several processes for the transesterification of triglycerides have been developed including the acid and base-catalyzed, homogeneous processes. Base-catalyzed reactions are simple and reasonably economical and, in fact, are used commercially in several countries for bio-diesel production and are described in J. Brazil. Chem. Soc. Vol. 9, Year 1998, pages 199 to 210; Bioresource Tech. Vol. 70, 1999, pages 1 to 15; Catalysis Vol. 19, 2006, pages 41 to 83; J. Am. Oil Chem. Soc. Vol. 75, 1998, pages 1775 to 1783; and U.S. Pat. Nos. 6,015,440 to Noureddini and 6,489,496 to Barnhorst et al. all of which are incorporated herein by reference. The use of alkali metal alkoxides may result in high yields of fatty acid alkyl esters in a short reaction time, however, alkali metal alkoxides may cause corrosion of components used in preparing the fatty acid alkyl acid esters. In addition to corrosion problems, these homogeneous catalyst-based processes involve elaborate process steps for removal of free fatty acids ("FFAs") and water from the feedstock and catalyst from the products. When FFAs are present, they react with the homogeneous alkali catalysts, form unwanted soap by-products, and deactivate the catalyst. In addition, water, sometimes present in non-edible, unrefined or waste vegetable oils also leads to the deactivation of homogeneous catalysts as described in Bioresource Tech. Vol. 70, 1999, pages 1 to 15. Separation and reuse of the homogeneous catalyst system is an issue needing additional process steps.

Several heterogeneous base and acid catalyst systems like metal oxides of tin, magnesium and zinc, Cs-MCM-41, Cs-exchanged NaX, ETS-10, Mg/Al hydrotalcites, alkali nitrate and alkali carbonate-loaded $Al_2O_3$, polymer resins, sulfated-tin and zirconia oxides and tungstated-zirconia have been reported for the transesterification of vegetable oil with alcohols are described in J. Am. Oil. Chem. Soc. Vol 78, 2001, page 1161; Bioresource. Technol. Vol. 70, 1999, pages 249 to 253; Appl. Catal. A: Gen. Vol. 218, 2001, pages 1 to 11; Catal. Today Vol. 93-95, 2004, pages 315 to 320; Green Chem. Vol. 6, 2004, pages 335 to 340; J. Mol. Catal. A: Chem. Vol. 109, 1996, pages 37 to 44;Appl. Catal. A: Gen. Vol. 257, 2004, pages 213 to 223; Ind. Eng. Chem. Res. Vol. 44, 2005, pages 7978 to 7082; Adv. Synth. Catal. Vol. 348, 2006, pages 75 to 81; Appl. Catal. A: Gen. Vol. 295, 2005, pages 97 to 105; J. Catal. Vol. 229, 2005, pages 365 to 373, all of which are incorporated herein by reference. Leaching of metal ions is encountered in a significant number of these heterogeneous systems. Free fatty acids, when present, inhibit the transesterification on solid basic catalysts, and, thereby, confine the catalyst systems to the transesterification of edible oils. Additional pre-treatment process steps are needed when using non-edible oils.

U.S. Pat. Nos. 5,908,946 to Stern; 6,147,196 to Stem et al.; and 6,878,837 to Bourna et al., all of which are incorporated herein by reference, describe the production of alkyl esters from vegetable and animal fat, and an aliphatic mono-alcohol in the presence of a heterogeneous zinc aluminate catalyst. Water inhibits this catalyst system and its presence in the reaction medium beyond an amount of 1000 ppm by weight is undesirable. U.S. Pat. No. 6,960,672 to Nakayama et al., which is incorporated herein by reference, describes the application of a catalyst that includes a composite metal oxide having a perovskite structure. The reaction was conducted by making alcohol into a supercritical state or subcritical state. U.S. Pat. No. 5,525,126 to Basu et al., which is incorporated herein by reference, describes the application of a mixture of calcium acetate and barium acetate. At the reaction conditions some amount of metal leaches into the liquid portion, hence, it is not a truly heterogeneously catalyzed system. U.S. Pat. No. 7,122,688 to Lin et al., which is incorporated herein by reference, describes the application of acidic mesoporous silicate for producing bio-diesel.

U.S. Pat. No. 5,713,965 to Foglia et al, which is incorporated herein by reference, describes the production of bio-diesel, lubricants and fuel and lubricant additives by transesterification of triglycerides with short chain alcohols in the presence of an organic solvent such as an alkane, an arene, a chlorinated solvent, or a petroleum ether using Mucor miehei or Candida Antarctica-derived lipase catalyst. International Patent Application Publication Nos. WO 00/05327 to Gnosar et al., WO 02/28811 to Koncar, WO 2004/048311 Muskett et al., WO 2005/021697 to Oku et al., and WO 2005/016560 to Hooker; and U.S. Pat. Nos. 5,578,090 to Bradin; 6,855,838 to Haas et al.; 6,822,105 to Luxen et al.; 6,768,015 to Luxem et al.; 6,712,867 to Boocock; 6,642,399 to Boocock; 6,399,800 to Haas et al.; 6,398,707 to Wu et al.; 6,015,440 to Noureddini, all of which are incorporated herein by reference, describe the production of fatty acid alkyl esters using either lipase catalysts or metal ion catalysts. International Patent Application Publication No. WO 2004/085583 describes transesterification of fats with methanol and ethanol in the presence of a solid acid catalyst having ultra-strong acid properties in a short time at around ambient pressure.

Production of diesel from pure soybean oil or coconut oil is not economical, so it is desirable to use cheaper alternative feedstock such as animal fat or used cooked oil or oil from seeds of wild plants like jojoba, jatropha or karanja. Animal fat and used oil contain high amounts of FFAs content. The FFAs saponifies with the alkali-based transesterification catalyst leading to low yield, difficulties in separation of the products, and increase in production cost. In those cases, a two step process in which during the first step an acid catalyst esterifies the free fatty acids to methyl esters and in the second step, transesterification of the triglycerides over a base catalyst is generally employed in diesel preparation.

Many methods and/or catalyst for the transesterification of fatty alkyl acids have been proposed, however, many conventional catalysts loose their activity on recycle and/or require pretreatment of the feedstock to remove the free fatty acids and water. Some conventional catalysts require harsh reaction conditions. Hence, an efficient, highly active catalyst capable of transesterifying both edible and non-edible vegetable oils in refined or unrefined forms at mild conditions is highly desirable. Such a catalyst system enables economic benefits and makes the bio-diesel and bio-lubricants an economical alternative to petroleum based diesel and lubricants.

SUMMARY

Embodiments described herein describe processes and catalyst for producing fatty acid alkyl esters. In certain embodiments, a process includes contacting one or more fatty acid glycerides with one or more alcohols in the presence of a catalyst to produce one or more reaction products; separating one or more of the reaction products from the catalyst; and separating one or more of the fatty acid alkyl esters from the reaction products. The catalyst includes one or more metal oxides and a promoter. At least one of the metal oxides includes a metal from Group VIB or Group IIIA of the Periodic Table. The promoter includes at least one element from Group VA of the Periodic Table.

DETAILED DESCRIPTION

Embodiments of methods described herein describe production of fatty acid alkyl esters. Such a fatty acid alkyl ester may be used as a bio-fuel, for example, bio-diesel, or a bio-lubricant. The processes described herein use a catalyst that has the added advantages of low cost and more run time life. In some embodiments, the catalyst is solid. In certain embodiments, the catalyst has acidic properties. The catalyst may be easily separated by centrifugation or by simple filtration (in case of a batch process) and may be re-used. Most importantly, the process is atom-efficient and the reaction conditions like temperature and pressure are only moderate. Unlike the conventional base catalysts, the catalyst of the present invention is more efficient even with non-edible oil containing free fatty acids and water impurity in oil. Thus, there are few limitations on the quality of oil that may be used with the catalysts of the present invention.

Methods described herein provide an efficient process for manufacturing of fatty acid alkyl esters (bio-diesel and bio-lubricants) in high yields at mild conditions. In some embodiments, the method is a single-step process for the production of bio-diesel and bio-lubricants from vegetable oils and fats containing significant amount of fatty acids.

In certain embodiments, methods to produce bio-diesel by transesterification of vegetable oil or fat with a $C_1$ to $C_4$ alcohol and bio-lubricants by transesterification with a $C_5$ to $C_{12}$ alcohol at moderate conditions and shorter reaction times either in a batch or fixed-bed process are described.

A heterogeneous supported catalyst suitable for the transesterification of fatty acid glycerides with added advantages of low cost catalysts considering the industrial economy and the stable systems with more run time life is described herein. As used herein, "heterogeneous catalyst" refers to a catalyst that is in a different phase (for example, a solid catalyst described herein) to other compounds (for example, liquid or vapor) when mixed together. The catalyst may be separated easily by centrifugation or by simple filtration (in the case of a batch process) and re-used.

In an embodiment, fatty acid glycerides of natural origin are contacted with alcohols in the presence of a heterogeneous supported catalyst to produce fatty acid alkyl esters. A mole ratio of fatty acid glyceride to alcohol may range from about 1:6 to 1:50, or from 1:10 to 1:40, or from 1:20 to 1:30. In certain embodiments, alcohols having 1 to 4 carbon atoms are reacted with fatty acid glycerides to form fatty acid alkyl ester suitable for use as a bio-diesel fuel. In an embodiment, the fatty acid alkyl ester made from contacting has 15 to 34 carbon atoms. In some embodiments, the mole percent conversion of fatty acid glycerides is 90 to 100 mol % and the bio-diesel/bio-lubricant selectivity is greater than 95%. Examples, of fatty acid alkyl esters made by the process described herein include, but are not limited to, alkyl esters of myristic, palmitic, palmitoleic, stearic, oleic, linoleic, linolenic, arachidic acids or mixtures thereof.

In some embodiments, the alcohols are primary alcohols. The alcohols may have from 1 to 50, from 2 to 25, or from 3 to 12 carbon atoms. Examples, of the alcohols include, but are not limited to, methanol, ethanol, propanol, butanol, pentanol, octanol, 2-ethylhexanol, decanol, dodecanol, or mixtures thereof.

The fatty acid glycerides may be obtained from vegetable oil, animal fat, or waste cooking oil. In some embodiments, the fatty acid glycerides include natural vegetable oils, for example coconut oil, palm oil, sunflower oil, soybean oil mustard oil, olive oil, cotton seed oil, rapeseed oil, margarine oil, jojoba oil, jatropha oil, karanja oil, or mixtures thereof.

In certain embodiments, catalyst includes one or more metals from Group VIB of the Periodic Table. The Group VIB metals may be inorganic salts (for example, nitrates, sulfates), and/or oxides. In some embodiments, the Group VIB metal is molybdenum or molybdenum oxide. An amount of Group VIB metal, calculated as metal by weight of catalyst, may range from about 0.01% to about 10%, from about 0.5% to 5%, or from 1% 5% Group VIB metal by weight of catalyst. An amount of Group VIB metal oxide may range from about 5% to about 20%, from about 8% to about 17%, or from about 10% to about 15% Group VIB metal oxide by weight of catalyst.

In some embodiments, the catalyst includes one or more metals from Group VIB of the Periodic Table described herein and a promoter. The promoter may be one of more elements from Group VA of the Periodic Table, for example, phosphorus or phosphorus compounds. In certain embodiments, the Group VA element (promoter) is a phosphorus compound. In an embodiment, the Group VA element is present in the range of about 0.1% to about 7%, about 0.5% to about 5%, about 1% to about 3% by weight of the catalyst.

In some embodiments, the catalyst includes one or more metals from GroupVIB of the Periodic Table described herein, a co-promoter and/or a promoter. The co-promoter may include metals or compounds of metals from Group IA of the Periodic Table, Group IIA of the Periodic Table, Group IIIB of the Periodic Table, Group VIII of the Periodic Table, or mixtures thereof. Examples of metals from Group IA, Group IIA, Group IIIB, or Group VIII of the Periodic Table include, but are not limited to, sodium, potassium, calcium, lanthanum, and nickel. An amount of co-promoter in the catalyst may range from about 0.0001% to about 10%, about 0.005% to about 8% or 0.5% to about 5% by weight of catalyst. In some embodiments, the catalyst may contain from about 0.05% to about 6.5% calcium by weight of the catalyst.

In some embodiments, the catalyst may include from 0.0001% to about 7.8% sodium and/or potassium by weight of the catalyst. In some embodiments, the catalyst may include from about 0.0001% to about 4.5% lanthanum by weight of catalyst. In some embodiments, the catalyst may include from 0.0001% to about 5.5% nickel by weight of catalyst.

The Group VIB metals, Group VIB metal compounds, promoters, co-promoters, or mixtures thereof may be supported on one or more oxides of one or more metals from Group IIIA of the Periodic Table. Examples of Group IIIA metal oxides (refractory oxides) include, but are not limited to, alumina oxide and/or titanium oxide. The refractory inorganic oxide may be of synthetic or natural origin and have a medium to a high surface area, and a well developed pore structure. In an embodiment, hydrated alumina, when used as a support material, results in a product where the morphology of the active materials is well maintained in the resulting catalyst composition.

The catalytic metals (for example, Group VIB metals) may be applied to a formed or unformed support by one of several methods known in the art. This is usually followed by forming, if necessary, and by calcinations to convert the catalytic metal compounds to oxides. U.S. Pat. Nos. 3,287,280 to Colgan et al. and 4,048,115 to O'Hara, both of which are incorporated herein by reference describe methods for the preparation of supported catalysts.

The intermediate support material of the catalyst may be prepared by either a solid mixing method or by a solution addition and subsequent mixing method. In both cases, the precursor of the support material (for example, alumina oxide) is well peptized with suitable mineral acid, for example, nitric acid and acetic acid. In an embodiment, nitric acid in the range of 1.0-10.0% of the support mass is used for peptization. The support precursor may be any of the Group IIIA or IVA refractory metal oxides or their combinations. In an embodiment, the Group IIIA metal oxide is alumina. In certain embodiments, a Group IIIA metal oxide is peptized with a mineral acid in the range of about 1% to about 10% or about 2% to 8%, or about 3% to about 7% by weight of the support material. For example, alumina oxide is peptized with nitric acid. In an embodiment, blending of various precursors of these metal oxides is performed to obtain suitable pore size distribution.

After peptization, active catalytic compounds, for example, metal oxides precursors of Group VIB, may be added along with the promoter selected from Group VA of the Periodic Table and/or co-promoter. In some embodiments, the co-promoter is added prior to forming the catalyst (for example, during extrusion), but before drying and/or calcination of the catalyst. The composition of the active metal, for example, molybdenum, may be incorporated using impregnation, compounding, extruding trials, various combinations of the processes described herein, or methods known in the art. A proper selection of appropriate preparation conditions may be made using methods known in the art. In some embodiments, the active metal precursor, the promoter precursor, and/or co-promoter may be added either as separate compounds or together as slurry. For example, the metal precursor and the promoter precursor may be combined by mixing two aqueous solutions together. An appropriate morphology and texture of the metal components may be achieved by applying suitable methods and combination of precursors. In an embodiment, the size and shape of the supported systems were to optimize, for example, tuning geometrical surface area. The surface area of the catalyst may range from 50 m$^2$/g to 300 m$^2$/g.

The catalyst may have a pore volume ranging from 0.2 ml/g to 0.95 ml/g, or from 0.5 ml/g to 0.7 ml/g. Pore volume of samples may be determined by filling the pore space to saturation by applying water. The quantity of water is determined by its volume added or the weight increase of the sample. The pore space can be filled by putting the quantitatively known sample in excess water and the excess water is removed, and the saturated catalyst samples were weighed again to determine the total water uptake.

In some embodiments, the catalyst composition resulting from the above described process may be directly shaped. Shaping includes extrusion, pelletizing, beading, and/or spray drying. In some embodiments, spray drying or beading is generally used when the catalyst composition is used in slurry type reactor, fluidized beds, moving beds, expanded beds, or ebullating beds. For fixed bed applications, the catalyst composition may be extruded, pelletized or beaded. In fixed bed applications, prior to or during the shaping, any additives that facilitate the shaping may be used.

The resulting catalyst composition or more suitably the catalyst intermediate may be, after an optional drying step, be optionally calcined. Calcinations temperatures may range from about 100° C. to 600° C. or from about 350° C. to 500° C. for a time varying from 0.5 to 48 hours. In certain embodiments, the catalyst samples are calcined at temperatures ranging from 400° C. to 500° C. or from 500° C. to 700° C.

The resultant extrudates may be further loaded with active metals to obtain the desired active metal composition for the finished product. Such further loading is directly related to the desired metal loading, and the amount incorporated during or prior to the shaping stage of the material. For the same, various impregnation methods known in the art can be applied. Either the wet impregnation or the incipient impregnation may be used to load active metals. In an embodiment, the pore filling incipient impregnation method may be applied to load the Group VI B metal oxides. The method employed also may affect the pore size distribution of the finished catalyst, and hence the performance of the product. The material is again to be further thermal treated for the activation of the catalytic components.

The supported catalysts described herein are highly efficient and are easily separated from the products for further re-use. In contrast, prior art catalysts may require treatment with mineral acid, alkali bases, and lipases which may increase costs of catalyst separation. The catalyst described herein is beneficial and leads to an economic and eco-friendly process. Hence, the solid catalysts described herein are not only efficient but avoid the tedious process of catalyst recovery characteristic of the prior art processes. The present catalyst system is efficient without using any additional solvent.

A process to produce fatty acid alkyl esters includes contacting a fatty acid glyceride, an alcohol, and a solid catalyst described herein to produce a reaction mixture. In some embodiments, the catalyst is a finely powdered catalyst. During contacting, the catalyst may remain in a separate phase, or substantially separate phase from the fatty acid glyceride, alcohol and/or reaction products. The catalyst may be separated from the liquid reaction mixture by separation techniques known in the art. For example, centrifugation followed by simple decantation. The resulting liquid reaction mixture may be separated by removal of excess alcohol through distillation techniques. Removal of the alcohol allows the fatty acid methyl esters to separate from remaining products. Fatty acid methyl esters may be separated from the reaction mixture by gravity separation or by contacting the reaction mixture with a non-polar solvent. In some embodiments, the non-polar solvent is petroleum ether.

The catalysts are prepared as described in EXAMPLES 1 to 11. Typical physicochemical characteristics of the selected catalysts prepared as described herein are listed in TABLE 1. In an embodiment, the catalyst material has a surface area ranging from 50 to 300 $m^2/g$, pore volume ranging from 0.2-0.95 ml/g and bulk density ranging from 0.4 to 1.3 g/ml.

TABLE 1

| Sample | Surface area ($m^2/g$) | Pore volume (ml/g) | Crush strength (kg) | Chemical composition[a], wt % | | |
|---|---|---|---|---|---|---|
| | | | | $MoO_3$ | P | Co-promoters (metal oxide) |
| Catalyst-1 | 295 | 0.52 | 6.6 | 14.78 | 0.03 | 0 |
| Catalyst-2 | 286 | 0.51 | 6.1 | 14.73 | 1.07 | 0 |
| Catalyst-3 | 270 | 0.55 | 5.1 | 14.88 | 2.04 | 0 |
| Catalyst-5 | 209 | 0.49 | 3.4 | 15.01 | 4.11 | 0 |
| Catalyst-6 | 184 | 0.57 | 3.7 | 15.16 | 3.02 | 0 |
| Catalyst-7 | 231 | 0.59 | 4.2 | 14.95 | 0.97 | 0 |
| Catalyst-8 | 179 | 0.51 | 4.7 | 14.81 | 2.89 | 4.82 ($Na_2O$) |
| Catalyst-9 | 187 | 0.53 | 4.5 | 14.41 | 2.74 | 4.76 ($K_2O$) |
| Catalyst-10 | 214 | 0.51 | 5.1 | 14.67 | 2.81 | 3.02 ($La_2O_3$) |
| Catalyst-11 | 243 | 0.61 | 3.9 | 14.12 | 0.99 | 0.97 (CaO) |
| Catalyst-12 | 220 | 0.62 | 4.1 | 14.02 | 2.87 | 3.01 (CaO) |
| Catalyst-13 | 228 | 0.61 | 5.2 | 14.97 | 2.96 | 1.04 (CaO) |
| Catalyst-14 | 197 | 0.52 | 4.8 | 14.82 | 4.09 | 2.07 (CaO) |
| Catalyst-15 | 208 | 0.57 | 4.7 | 14.77 | 2.99 | 3.11 (NiO) |

[a]Balance refractory oxides.

It is a feature of the process of described herein is a single step process. Thus, the requirement for the saponification step in conventional processes is not necessary. Other features of the process described herein are that the catalyst is a solid and the reaction takes place in a heterogeneous condition, the product bio-diesel and bio-lubricant is a liquid and the solid catalyst is easily separated from products by centrifugation/filtration for further re-use. Another advantage of the process described herein is that the reaction is conducted using minimal or substantially no solvent. In an embodiment, the reaction is conducted in the absence of solvent. Another advantage of the process described herein is that the catalyst is highly selective which results in increased glycerol purity and fatty acid methyl ester yield as compared to products produced using conventional catalyst. The process described herein also reduces the formation of undesirable impurities, for example, glycerol ethers.

EXAMPLES

Non-limiting examples are described herein.

Example-1

Preparation of a catalyst support and Catalyst 1 is described herein. Hydrated alumina (containing 0.83 moles of alumina) was mix mulled with ammonium heptamolybdate (0.00741 moles) after the peptization with a suitable mineral acid. The material was extruded to 1.2 mm extrudates and the sample, after an optional drying, calcined at 400° C. to 500° C.

The alumina sample was impregnated with an aqueous solution of ammonium heptamolybdate (0.00712 moles) using the pore filling impregnation method for further metal loading. After optional drying, the sample was calcined at 400° C. to 500° C. for 4 hrs. This sample was designated as Catalyst 1.

Example-2

Catalyst 2 was prepared using the method described in Example 1, except that an additional promoter was introduced to the final catalyst composition. Phosphoric acid (0.0322 moles) in addition to the ammonium heptamolybdate was added during the mix mull stage of the support preparation. The resulting material was extruded to 1.2 mm, calcined at 400° C. to 500° C. for 4 hrs, and impregnated with a solution of ammonium heptamolybdate (0.00712 moles). After optional drying, the material was subjected to a final calcination at 400° C. to 500° C. for 4 hrs.

Example-3

Catalysts 3, 4, and 5 were prepared using the preparation described in Example-2, except that the quantity of phosphoric acid was varied (0.0654 moles of phosphoric acid for Catalyst 3, 0.0968 moles of phosphoric acid for Catalyst 4, and 0.1308 moles of phosphoric acid for Catalyst 5). After optional drying, the material was subject to a final calcination at 400° C. to 500° C. for 4 hrs.

Example-4

Catalysts 6 and 7 were prepared using the preparation described in Example-2, except that the quantity phosphoric acid was varied (0.0968 moles of phosphoric acid for Catalyst 6, and 0.0322 moles of phosphoric acid for Catalyst 7). After optional drying, the material was subject to a final calcination at 500° C. to 700° C. for 4 hrs.

Example-5

Catalyst 8 was prepared using the preparation described in Example 2, except the amount of phosphoric acid (0.0968 moles) varied, di-sodium monoxide (0.080645 moles) was added during the support preparation. After optional drying, the sample was calcined at 500° C. to 700° C. for 4 hrs.

Example-6

Catalyst 9 was prepared using the preparation described in Example 2, except that the amount of phosphoric acid (0.0968 moles) varied and di-potassium monoxide (0.05319 moles) was added during the support preparation. After optional drying, the sample was calcined at 500° C. to 700° C. for 4 hrs.

Example-7

Catalyst 10 was prepared using the preparation described in Example 2, except that the amount of phosphoric acid (0.0968 moles) varied and lanthanum trioxide (0.009202 moles) was added during the support preparation. After optional drying, the sample was calcined at 500° C. to 700° C. for 4 hrs.

Example-8

Catalysts 11 and 12 were prepared using the preparation described in Example 2, except that the amount of phosphoric acid (0.0322 moles) varied and a solution of calcium nitrate was added before extrusion. For the preparation of Catalyst 11, the solution of calcium nitrate contained 0.01785 moles of calcium oxide. For the preparation of Catalyst 12, the solution of calcium nitrate contained 0.05356 moles of calcium oxide. After optional drying, the samples were calcined at 500° C. to 700° C. for 4 hrs.

Example-9

Catalyst 13 was prepared using the preparation described in Example 2, except that the amount of phosphoric acid (0.0968 moles) varied and lanthanum trioxide (0.009202 moles) was added during the support preparation. After optional drying, the sample was calcined at 500° C. to 700° C. for 4 hrs.

Example-10

Catalyst 14 was prepared using the preparation described in Example 5, except that that an aqueous solution of calcium nitrate containing 0.0357 moles of calcium oxide was incorporated during the mix mull stage. After optional drying, the sample was calcined at 500° C. to 700° C. for 4 hrs.

Example-11

Catalyst 15 was prepared using the preparation described in Example 2, except that the amount of phosphoric acid (0.0968 moles) varied, and nickel oxide (0.04005 moles) was added during the support preparation. After optional drying, the sample was calcined at 500° C. to 700° C. for 4 hrs.

Example-12

All the catalyst samples were evaluated for pore volume measurement by filling the pore space to saturation with water as well as by a mercury penetration method. Also the samples were evaluated for their mechanical strength to see the tolerance to actual operation conditions, where a pressure drop in the system indicates the breakage of the catalyst sample. All the catalyst samples were evaluated for BET surface area values through the $N_2$ adsorption method. Also the samples were characterized for molybdenum content and phosphorous content. The data for Catalysts 1-15 are listed in TABLE 1.

Example-13

Selected catalyst samples were tested, for evaluation of their active metal and promoter leaching. Molybdenum (active metal), phosphorous (promoter), and co-promoters, if present, were considered. The evaluation was performed by refluxing a catalyst sample with 1:1 mixture of methanol and oleic acid for 4 hrs in a distillation set up and quantitatively analyzing the filtrates for molybdenum content, phosphorous content, and co-promoter content, if present.

Example-14

Selected catalyst samples were selected for activity and performance evaluations. Screening of the samples was done based on the physico-chemical properties, mainly the intrinsic properties and the leaching issues. Samples with improved physico-chemical properties and minimum leaching of active phase/promoters are considered for further evaluations. Activity/performance evaluations of the samples were done, by using Teflon-lined stainless steel/batch reactors and fixed bed reactors at temperatures ranging from 150° C. to 250° C. and pressures ranging from 10 to 40 bars, along with the reactants soybean oil and methanol in various mole ratios of 6 to 40. The reaction mixture was collected at various intervals and tested for the conversion to fatty acid methyl esters. A purity of glyercol was determined.

A typical batch reaction for producing fatty acid methyl esters (bio-diesel) from sunflower oil and methanol was conducted in a "Teflon-lined" steel autoclave (100 ml) and using a rotating hydrothermal reactor (Hiro Co., Japan; Mode- KH 02). The rotation speed was 50 rpm. A known quantity of vegetable oil, alcohol and "finely powdered" solid catalyst were taken in a sealed reactor and the reaction was conducted at a desired temperature for a desired period of time. The autoclaves were cooled to room temperature. The catalyst was separated by centrifugation followed by simple decantation. The entire liquid was subjected to vacuum distillation and excess, unused alcohol was removed. Glycerol settled at the bottom as a separate layer. Fatty acid methyl esters and un-reacted oil, if any, floated above the glycerol portion. Petroleum ether (20 to 50 ml) was then, added. The esters and oil readily went into the petroleum ether layer. Glycerol remained as a separate layer. It was separated and its yield was determined and purity checked by $^1H$ nuclear magnetic resonance (Bruker 200 MHz Avance NMR spectrometer). Fatty acid alkyl ester portion was analyzed by high performance liquid chromatography (HPLC) and gas chromatography (GC) techniques. Results of various experiments conducted at different reaction conductions and using catalysts of the present invention are listed in TABLE 2.

Example-15

The preparation of fatty acid methyl esters (bio-diesel) from unrefined non-edible karanja oil and methanol is described herein. The reaction was conducted in a similar manner as described in EXAMPLE-14 except that karanja oil without purification was used instead of edible sunflower oil. Unrefined karanja contained about 6 wt % of free fatty acid and significant quantities of water impurities in the feed. The results of the reaction as analyzed by HPLC are listed in TABLE 2. Perkin-Elmer Series 200 HPLC fitted with a reverse-phase, C-18 Spheri-5 column (250×4.6 mm with a 5 μm particle size) and ELSD detector (Gilson) was used for the HPLC analysis. An injection volume of 10 microliters, flow rate of 1 ml/min, column temperature of 50° C., and mobile phase of methanol and 2-propanol/n-hexane (5:4 v/v) were employed. The resulting glycerol had a purity of 90- 98% as determined by gas chromatography (GC). A Varian GC instrument (injector at 250° C. and detector at 260° C.) equipped with Varian Select for FAME column (30 m×0.32 mm ID×0.25 μm film thickness) was employed in the analysis.

Example-16

The preparation of fatty acid methyl esters from soybean oil and methanol in a fixed-bed reactor is described herein. In a typical fixed-bed reaction a bed of catalyst in the form of extrudates is placed in a stainless steel reactor having a provision of auto-controlled temperature and feed-flow facilities. As methanol and oil are immiscible, a duel pumping system was utilized and the feed was sent in an upward-flow at a regulated flow rate. The product was collected from the top of the reactor and the bio-diesel was isolated in a similar manner as described in EXAMPLE-14. TABLE 3 lists the operating conditions and product composition (wt % as determined by HPLC analysis) of reacting soybean oil or karanja oil and methanol in a fixed-bed reactor over Catalyst-13 at a methanol: oil molar ratio of 15. Perkin-Elmer Series 200 HPLC fitted with a reverse-phase, C-18 Spheri-5 column (250×4.6 mm with a 5 μm particle size) and ELSD detector (Gilson) was used for the HPLC analysis. An injection volume of 10 microliters, flow rate of 1 ml/min, column temperature of 50° C., and mobile phase of methanol and 2-propanol/n-hexane (5:4 v/v) were employed.

TABLE 3

| Oil | Pressure, bar | Temp., °C. | WSHV, hr$^{-1}$ | Product composition, wt % by HPLC analysis | | | |
|---|---|---|---|---|---|---|---|
| | | | | Tri-glyceride | Di-glyceride | Mono-glyceride | Fatty acid methyl ester |
| Soybean | 55 | 240 | 0.4 | 0.6 | 0.6 | 2.2 | 96.6 |
| Soybean | 55 | 240 | 1.8 | 9.4 | 1.8 | 3.3 | 85.5 |
| Soybean | 30 | 215 | 0.4 | 9.9 | 2.6 | 4.1 | 83.4 |
| Karanja | 55 | 215 | 0.4 | 4.4 | 10.7 | 13.7 | 71.2 |

Example-17

1 The production of fatty acid octyl esters for bio-lubricants from soybean oil and octanol in a fixed-bed reactor is described herein. Higher alcohols such as octanol and oil are miscible. The feed was prepared and fed to the reactor using a single pump and the reaction and work-up were conducted in a similar manner as described in Example-14. TABLE 4 lists the results of the reacting soybean oil and octanol in a fixed-bed reactor at a octanol to soybean oil molar ratio of 15. The resulting glycerol had a purity of 90-98% determined by the GC technique using conditions described in the Example 15.

TABLE 4

| Catalyst, | Pressure bar | Temp. °C. | WSHV hr$^{-1}$ | Product composition, wt %, by HPLC analysis | | | |
|---|---|---|---|---|---|---|---|
| | | | | Tri-glyceride | Di-glyceride | Mono-glyceride | Fatty acid octyl ester |
| Catalyst-2 | 30 | 220 | 0.2 | 13.1 | 0.3 | 0.5 | 86.4 |
| Catalyst-4 | 20 | 220 | 0.4 | 20 | 1.2 | 0.4 | 78.2 |
| Catalyst-4 | 20 | 240 | 0.4 | 6.5 | 2.5 | 0.6 | 90.4 |
| Catalyst-13 | 20 | 240 | 0.4 | 4.0 | 2.0 | 0.5 | 93.5 |

Example-18

The production of fatty acid methyl esters (bio-diesel) by esterification of oleic acid with methanol is described herein. The reaction was conducted in a similar manner as described in the EXAMPLE-14 taking oleic acid and methanol in a molar ration of 1:5. The bio-diesel yield was 97% as determined by the GC analysis described in EN14103.

Example-19

The production of fatty acid octyl esters (bio-lubricant) by esterification of oleic acid with octanol is described herein. The reaction was conducted in a similar manner as described in the EXAMPLE-14 taking oleic acid and octanol in a molar ration of 1:5. The octyl ester (bio-lubricant) yield was 95% as determined by the GC analysis described in EN14103.

Example-20

The production of fatty acid methyl esters (bio-diesel) by reaction of soybean oil with an equimolar mixture of methanol and ethanol over Catalyst- 13. The reaction was conducted in a similar manner as described in the EXAMPLE-14. The conversion of soybean oil was 99.5% and fatty acid methyl/ether esters yield was 92% as determined by HPLC analysis. Perkin-Elmer Series 200 HPLC fitted with a reverse-phase, C-18 Spheri-5 column (250×4.6 mm with a 5 μm particle size) and ELSD detector (Gilson) was used for the HPLC analysis. An injection volume of 10 microliters, flow rate of 1 ml/min, column temperature of 50° C., and mobile phase of methanol and 2-propanol/n-hexane (5 to 4 v/v) were employed.

Advantages of the process and catalysts described herein include: 1) the process has the combined unique advantages of high conversion accompanied with high selectivity for fatty acid alkyl esters; 2) no issues related to saponification are encountered and the catalyst is reused several times and in long time on stream studies; and 3) the catalyst of the present invention is highly efficient for the preparation of bio-diesel (from vegetable oil or fat and $C_1$ to $C_4$ alcohols) and bio-lubricants (from vegetable oil or fat and $C_5$ to $C_{12}$ alcohols).

Reference Catalyst. A reference catalyst sample was prepared as described in U. S. Patent Application Publication No. 2007/0004599 to Darbha et al, which is incorporated herein by reference. The reference catalyst sample was a double metal cyanide catalyst, prepared by the reaction of potassium ferrocyanide in aqueous media and zinc chloride using tertiary butyl alcohol, followed by the addition of a co-complexing agent of polyethylene glycol 4000. The resulting powder sample was used for comparison of activity/performance of the catalysts described herein. The reference catalyst sample was designated as Catalyst-R.

In this patent, certain U.S. patents, U.S. patent applications, and other materials (for example, articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. In addition, it is to be understood that features described herein independently may, in certain embodiments, be combined.

separating one or more of the reaction products from the catalyst; and separating one or more of the fatty acid alkyl esters from the reaction products.

2. The process of claim 1, wherein at least one of fatty acid alkyl esters is an alkyl ester of myristic, palmitic, palmitoleic, stearic, oleic, linoleic, linolenic, arachidic acids and mixtures thereof.

3. The process of claim 1, wherein at least one of the fatty acid glycerides is obtained from a vegetable oil, an animal fat, or a waste cooking oil.

4. The process of claim 1, wherein at least one of the fatty acid glycerides is selected from the group consisting of coconut oil, palm oil, sunflower oil, soybean oil, mustard oil, olive oil, cotton seed oil, rapeseed oil, margarine oil, jojoba oil, jatropha oil, karanja oil, and mixtures thereof.

5. The process of claim 1, wherein at least one of the alcohols is selected from the group consisting of methanol, ethanol, propanol, butanol, pentanol, octanol, 2-ethylhexanol, decanol, dodecanol, and mixtures thereof.

6. The process of claim 1, wherein at least one of the alcohols has a carbon number ranging from 1 to 50.

TABLE 2

| Catalyst (wt % of oil) | Type of oil/fat (grams) | Alcohol | Alcohol to oil molar ratio | Temp., °C. | Reaction time, hr | Oil/fat conversion wt % | Product composition, wt % - HPLC analysis | | | |
|---|---|---|---|---|---|---|---|---|---|---|
| | | | | | | | Tri-glyceride | Di-glyceride | Mono-glyceride | Fatty acid methyl ester |
| Catalyst-2 (5) | Soybean (33) | Methanol | 15 | 190 | 8 | 97.2 | 2.8 | 7.1 | 3.2 | 90.1 |
| Catalyst-4 (5) | Soybean (33) | Methanol | 15 | 190 | 8 | 100 | 0 | 0.5 | 4.0 | 95.6 |
| Catalyst-7 (10) | Sunflower (15) | Methanol | 25 | 200 | 6 | 100 | 0 | 2.1 | 0.9 | 97.0 |
| Catalyst-7 (10) | Sunflower (15) | Methanol | 40 | 200 | 6 | 100 | 0 | 0 | 1.0 | 99.0 |
| Catalyst-10 (10) | Soybean (15) | Methanol | 15 | 190 | 8 | 100 | 0 | 2.8 | 4.8 | 92.3 |
| Catalyst-13 (10) | Soybean (15) | Methanol | 15 | 190 | 8 | 100 | 0 | 1.2 | 9.7 | 89.7 |
| Catalyst-13 (10) | Karanja (15) | Methanol | 15 | 190 | 8 | 100 | 0 | 11.9 | 19.9 | 68.1 |
| Catalyst-13 (10) | Palm (15) | Methanol | 15 | 190 | 8 | 99.7 | 0.3 | 3.9 | 14.4 | 81.9 |
| Catalyst-13 (10) | Chicken fat (15) | Methanol | 15 | 190 | 8 | 99.9 | 0.1 | 0.8 | 10.8 | 88.4 |
| Catalyst-13 (5) | Soybean (5) | Octanol | 12 | 200 | 8 | 99.2 | 0.8 | 0 | 8.1 | 91.2 |
| Catalyst-15 (10) | Soybean (15) | Methanol | 15 | 190 | 8 | 100 | 0 | 0.06 | 3.2 | 96.2 |
| Catalyst-R (5) | Sunflower (15) | Methanol | 15 | 190 | 2 | 97.2 | 2.8 | 4.4 | 1.5 | 91.4 |
| Catalyst-R (10) | Sunflower (15) | Methanol | 15 | 200 | 2 | 100 | 0 | 1.3 | 5.2 | 93.6 |

What is claimed is:

1. A process of producing one or more fatty acid alkyl esters, comprising:

contacting one or more fatty acid glycerides with one or more alcohols in the presence of a catalyst to produce one or more reaction products, wherein the catalyst comprises one or more metal oxides and a promoter, wherein at least one of the metal oxides comprises one or more metals from Group VIB of the Periodic Table, wherein at least one metal from Group VIB of the Periodic Table comprises molybdenum, and wherein the promoter comprises at least one element from Group VA of the Periodic Table;

7. The process of claim 1, wherein the molar ratio of fatty acid glyceride to alcohol is in the range of 1:6 to 1:50.

8. The process of claim 1, wherein contacting is conducted at a temperature in the range of 150° C. to 250° C.

9. The process of claim 1, wherein the catalyst further comprises a metal from Group IIIA of the Periodic Table, and wherein the metal from Group IIIA comprises aluminum.

10. The process of claim 1, wherein the element from Group VA of the Periodic Table comprises phosphorous.

11. The process of claim 1, wherein at least one of the fatty acid alkyl esters comprises a bio-diesel.

12. The process of claim 1, wherein at least one of the fatty acid alkyl esters comprises a bio-lubricant.

13. The process of claim 1, wherein at least one of the fatty acid alkyl esters comprises a bio-fuel.

14. The process of claim 1, wherein separating one or more of the fatty acid alky esters from the one or more reactions products comprises contacting the one or more reaction products with a non-polar solvent.

15. The process of claim 1, wherein the catalyst further comprises a co-promoter, wherein the co-promoter comprises one or more metals from Group IA of the Periodic Table.

16. The process of claim 1, wherein the catalyst further comprises a co-promoter, wherein the co-promoter comprises one or more metals from Group IIA of the Periodic Table.

17. The process of claim 1, wherein the catalyst further comprises a co-promoter, wherein the co-promoter comprises one or more metals from Group IIIB of the Periodic Table.

18. The process of claim 1, wherein the catalyst further comprises a co-promoter, wherein the co-promoter comprises one or more metals from Group VIII of the Periodic Table.

19. The process of claim 1, wherein the catalyst further comprises a co-promoter, wherein the co-promoter comprises calcium.

20. The process of claim 1, wherein the catalyst further comprises a co-promoter, wherein the co-promoter comprises potassium.

21. The process of claim 1, wherein the catalyst further comprises a co-promoter, wherein the co-promoter comprises lanthanum.

22. The process of claim 1, wherein the catalyst further comprises a co-promoter, wherein the co-promoter comprises nickel.

23. The process of claim 1, wherein the catalyst is a solid acid catalyst.

24. The process of claim 1, wherein catalyst remains as a separate phase or a substantially separate phase during contacting.

25. A process of manufacturing of fatty acid alkyl esters, comprising:
 contacting one or more fatty acid glycerides with one or more alcohols in the presence of a catalyst to produce one or more reaction products, wherein the catalyst comprises one or more metal oxides, a promoter, and a co-promoter, wherein at least one of the metal oxides comprises a metal from Group VIB of the Periodic Table, wherein at least the promoter comprises at least one element from Group VA of the Periodic Table and wherein the co-promoter comprises one or more metals from Group IIA of the Periodic Table;
 separating one or more of the reaction products from the catalyst; and
 separating one or more of the fatty acid alkyl esters from the reaction products.

26. The process of claim 25, wherein at least one of fatty acid alkyl esters is an alkyl ester of myristic, palmitic, palmitoleic, stearic, oleic, linoleic, linolenic, arachidic acids and mixtures thereof.

27. The process of claim 25, wherein at least one of the fatty acid glycerides is obtained from a vegetable oil, an animal fat, or a waste cooking oil.

28. The process of claim 25, wherein at least one of the fatty acid glycerides is selected from the group consisting of coconut oil, palm oil, sunflower oil, soybean oil, mustard oil, olive oil, cotton seed oil, rapeseed oil, margarine oil, jojoba oil, jatropha oil, karanja oil, and mixtures thereof.

29. The process of claim 25, wherein at least one of the alcohols is selected from the group consisting of methanol, ethanol, propanol, butanol, pentanol, octanol, 2-ethylhexanol, decanol, dodecanol, and mixtures thereof.

30. The process of claim 25, wherein at least one of the alcohols has a carbon number ranging from 1 to 50.

31. The process of claim 25, wherein the molar ratio of fatty acid glyceride to alcohol is in the range of 1:6 to 1:50.

32. The process of claim 25, wherein contacting is conducted at a temperature in the range of 150 ° C. to 250 ° C.

33. The process of claim 25, wherein at least one of the metals from Group VIB of the Periodic Table comprises molybdenum.

34. The process of claim 25, wherein the element from Group VA of the Periodic Table comprises phosphorous.

35. The process of claim 25, wherein separating one or more of the fatty acid alky esters from the one or more reactions products comprises contacting the one or more reaction products with a non-polar solvent.

36. The process of claim 25, wherein at least one of the metals from Group IIA of the Periodic Table comprises calcium.

37. The process of claim 25, wherein the catalyst is a solid acid catalyst.

38. The process of claim 25, wherein catalyst remains as a separate phase or a substantially separate phase during contacting.

39. The process of claim 25, wherein at least one of the fatty acid alkyl esters comprises a bio-diesel.

40. The process of claim 25, wherein at least one of the fatty acid alkyl esters comprises a bio-lubricant.

41. The process of claim 25, wherein at least one of the fatty acid alkyl esters comprises a bio-fuel.

42. A process of producing one or more fatty acid alkyl esters, comprising:
 contacting one or more of the fatty acid glycerides with one or more of the alcohols in the presence of a catalyst to produce one or more reaction products, wherein the catalyst comprises one or more metal oxides and a promoter on a support, wherein at least one of the metal oxides comprises one or more metals from Group VIB of the Periodic Table, wherein at least one metal from Group VIB comprises molybdenum, and wherein the promoter comprises at least one element from Group VA of the Periodic Table;
 separating one or more of the reaction products from the catalyst; and
 separating one or more of the fatty acid alkyl esters from the reaction products.

43. The process of claim 42, wherein the element from Group VA of the Periodic Table comprises phosphorous.

44. The process of claim 42, wherein the catalyst further comprises a co-promoter, wherein the co-promoter comprises one or more metals from Group IIA of the Periodic Table.

45. The process of claim 42, wherein the catalyst further comprises a co-promoter, wherein the co-promoter comprises calcium.

46. The process of claim 42, wherein the support comprises one or more metals oxides from Group IIIA.

47. The process of claim 42, wherein the support further comprises alumina.

48. The process of claim 42, wherein at least one of the fatty acid alkyl esters comprises a bio-diesel.

49. The process of claim 42, wherein at least one of the fatty acid alkyl esters comprises a bio-lubricant.

50. The process of claim 42, wherein at least one of the fatty acid alkyl esters comprises a bio-fuel.

51. A process of producing one or more fatty acid alkyl esters, comprising:
 contacting one or more fatty acid glycerides with one or more alcohols in the presence of a catalyst to produce one or more reaction products, wherein the catalyst comprises one or more metal oxides and a promoter, wherein at least one of the metal oxides comprises one or more metals from Group VIB of the Periodic Table in an amount of metal by weight of the catalyst ranging from about 0.01% to about 20%, and wherein the promoter comprises at least one element from Group VA of the Periodic Table present in the range of about 0.1% to about 7% by weight of the catalyst;

separating one or more of the reaction products from the catalyst; and separating one or more of the fatty acid alkyl esters from the reaction products.

52. The process of claim 51, wherein the element from Group VA of the Periodic Table comprises phosphorous.

53. The process of claim 51, wherein the catalyst further comprises a co-promoter, wherein the co-promoter comprises one or more metals from Group IIA of the Periodic Table.

54. The process of claim 51, wherein the catalyst further comprises a co-promoter, wherein the co-promoter comprises calcium.

55. The process of claim 51, wherein the catalyst further comprises one or more metals oxides from Group IIIA.

56. The process of claim 51, wherein at least one of the alcohols has a carbon number ranging from 1 to 50.

57. The process of claim 51, wherein the molar ratio of fatty acid glyceride to alcohol is in the range of 1:6 to 1:50.

58. The process of claim 51, wherein at least one of the fatty acid glycerides is obtained from a vegetable oil, an animal fat, or a waste cooking oil.

59. A process of producing one or more fatty acid alkyl esters, comprising:

contacting one or more fatty acid glycerides with one or more alcohols in the presence of a catalyst to produce one or more reaction products, wherein the catalyst comprises one or more metal oxides and a promoter, wherein at least one of the metal oxides comprises one or more metals from Group VIB of the Periodic Table, wherein at least one metal from Group VIB of the Periodic Table comprises molybdenum, and wherein the promoter comprises at least one element from Group VA of the Periodic Table;

separating one or more of the reaction products from the catalyst by contacting the one or more reaction products with a non-polar solvent; and separating one or more of the fatty acid alkyl esters from the reaction products.

* * * * *